(12) United States Patent
Alawadi

(10) Patent No.: US 8,395,119 B2
(45) Date of Patent: Mar. 12, 2013

(54) AIRBORNE/SPACEBORNE OIL SPILL DETERMINING SYSTEM

(76) Inventor: Fahad A. M. I. Alawadi, Qortuba (KW)

( * ) Notice: Subject to any disclaimer, the term of this patent is extended or adjusted under 35 U.S.C. 154(b) by 746 days.

(21) Appl. No.: 12/611,312

(22) Filed: Nov. 3, 2009

(65) Prior Publication Data

US 2011/0101225 A1 May 5, 2011

(51) Int. Cl.
*G01J 5/02* (2006.01)
*G01T 1/167* (2006.01)
*G01T 1/00* (2006.01)
*G01V 5/00* (2006.01)

(52) U.S. Cl. ............... 250/339.02; 250/301; 250/253; 250/336.1

(58) Field of Classification Search .......... 250/301, 250/253, 336.1, 339.02
See application file for complete search history.

(56) References Cited

U.S. PATENT DOCUMENTS

| | | | |
|---|---|---|---|
| 3,899,213 A | 8/1975 | Fantasia et al. | |
| 5,296,711 A | 3/1994 | Leonard et al. | |
| 5,450,125 A | 9/1995 | Ulich et al. | |
| 5,471,056 A | 11/1995 | Prelat | |
| 6,784,428 B2 | 8/2004 | Rabolt et al. | |
| 7,417,228 B2 | 8/2008 | Belov et al. | |
| 8,044,342 B2 * | 10/2011 | Galford et al. | 250/269.6 |
| 2009/0039255 A1 * | 2/2009 | Andrews et al. | 250/301 |

OTHER PUBLICATIONS

Fahad Alawadi, Carl Amos, Valborg Byfield, Peter Petrov, The Application of Hyperspectral Image Techniques on MODIS data for the detection of oil spills in the RSA, SPIE vol. 7110 71100Q-1, Oct. 2008.

* cited by examiner

*Primary Examiner* — David Porta
*Assistant Examiner* — Faye Boosalis
(74) *Attorney, Agent, or Firm* — Lowe Hauptman Ham & Berner, LLP

(57) ABSTRACT

An airborne/spaceborne oil spill detection method includes the step of providing a moderate-resolution-imaging-spectroradiometer and sensing the spectral reflections from two optical bands one of which is in the near infrared range. The spectral contrast shift from two adjacent areas of water are calculated and a warning issued when an oil spill or other contaminant is detected. A system for detecting an oil spill or other contaminant on the surface of water is also disclosed.

2 Claims, 3 Drawing Sheets ns on a water surface.
AIRBORNE/SPACEBORNE OIL SPILL DETERMINING SYSTEM

FIELD OF THE INVENTION

This invention relates to an airborne/spaceborne oil spill determining system and more particularly to an airborne/spaceborne oil spill detection system for detecting oil spills and other contaminants on a water surface.

BACKGROUND FOR THE INVENTION

There are many known techniques for the remote sensing of oil spills in a marine environment. Such methods operate in various parts of the electromagnetic spectra including passive and active methods many of which utilize expensive special design detector systems and depend on illumination geometry of the scene.

An example of an Airborne Scanner Image spectrometer is disclosed in a U.S. Patent of Prelat, U.S. Pat. No. 5,471,056. As disclosed an airborne multi-spectral sensor system utilizes real time acquisition of images in many narrow, continuous spectral bands, to generate hyper-spectral image data and in particular to image data sets which can be used individually or combined to get spectral profiles and emittance to identify ground targets.

As disclosed in the above-identified patent, an airborne sensor processing unit includes a first plurality of spectrometers forming a first continuous selectable band from 400 to 1140 nanometers, a second plurality of spectrometers forming a second continuous band from 1400 to 2500 nanometers and a thermal sensor array formed with two configurations with the first having at least six bands running from 8.40 to 11.70 µm and the second having at least seven bands from 8.35 to 11.45 µm. The three spectrometers are each connected to receive input from a single discriminator having a plurality of optical sensors of known type. These sensors provide optical imaging for a known field of view which at a given known altitude will cover a determinable width.

A second reference of Belov et al., U.S. Pat. No. 7,417,228 discloses a device for detecting oil pollution on water surfaces. The method of detecting oil pollution on water surfaces includes the step of providing echo signals obtained from optical radiation of a clean water area two wavelengths and optically radiating an investigated water area at two wavelengths. The method also includes the step of obtaining echo signals from the optical radiation of the investigated water area at the two wavelengths and comparing the echo signals obtained form the radiation of the investigated area and two wavelengths with the echo signals obtained from the radiation of the clean water area then, based on the comparison, determining the presence or absence of an oil pollution in the investigated water area. The aforementioned patent also discloses a device for detecting oil pollution that includes means for optically radiating an investigated water area at two wavelengths and obtaining echo signals from the optical radiation of the investigated water area, means for comparing the echo signals obtained from the radiation of the investigated area at two wavelengths with the echo signals obtained form the radiation of the clean water surface area and means from determining the presence or absence of oil pollution in the investigated water area.

Notwithstanding the above, it is presently believed that there is a need and a potential commercial market for an airborne system for detecting oil spills and other contaminants on a water surface in accordance with the present invention. There should be a commercial market for such system because such systems utilize standard resolution band 1 and band 2 information from a moderate resolution imaging spectroradiometer/MODIS or similar optical scanner facility including airborne units. Then due to the difference behavior of band 1 and band 2 after real-time processing a warning will be enabled to indicate an oil spill or some other contaminates on the sea surface. In addition, such systems can be used to identify and call immediate attention to areas where significant concentrations of oil or related contaminants are encountered.

BRIEF SUMMARY OF THE INVENTION

In essence, an airborne/spaceborne oil spill determining method for detecting oil spills on a water surface include the following steps:

providing a moderate-resolution imaging spectroradiometer for detecting a wide spectral range of electromagnetic energy and sensing the spectral reflections from two optical bands wherein one of the bands is within the near infrared range and the other of the bands is outside of the near infrared range. Bands result from an area of water suspected of oil contamination and from an adjacent area of clear water;

calculating the spectral contrast shift on-site and in real-time from both bands.

issuing a warning in response to an oil spill or other contaminants floating on the water surface.

In a preferred embodiment of the invention the spectral contrast shift (SCS) is calculated on-site and in real time from both bands wherein SCS equals $[(L_{max2}/L_{max1})-(L_{min2}/L_{min1})]$ The invention also contemplates an airborne oil spill detection system for detecting oil spills and other contaminants on a water surface. The system includes a moderate resolution imaging spectrometer providing high radiometric sensitivity in two spectral bands $L_1$ and $L_2$ ranging in wavelength from 0.4 µm to 14.4 µm and wherein one of the bands is within the infrared range and the other of the bands is outside of the infrared range. The system also includes an initialization controller for synchronizing the system operation and inputting cloud and land mask signals. Further, a pair of enable/disable gates to enable the reception of bands $B_1$ and $B_2$ over areas where no clouds or land exist, or to disable their reception when cloud cover or land exist over the area. In addition the enabled/disabled gates enable band data to be processed further when cloudless conditions exist. A pair of extreme value units for calculating the respective extreme value exceeding a programmed threshold from the data flow from $B_1$ and $B_2$.

The invention will now be described in connection with the accompanying drawings wherein like reference numerals have been used to indicate like parts.

DESCRIPTION OF THE PREFERRED EMBODIMENTS OF THE INVENTION

A method for oil pollution and other contaminants on water surfaces in accordance with the present invention is based on calculating the spectral passive reflection response from two optical bands. One of the bands is in the near infrared (NIR) band while the other band is outside of the NIR band i.e. in the visual band. One of the bands is taken from the surface of water that is suspected of having pollution while the other is from an adjacent area that is believed to be clear water. The 250 m resolution bands one and two belonging to the Moderate Resolution Imaging Spectroradiometer (MODIS) can be implemented in the device or by means of a similar passive optical scanner and from various platforms. According to a constant value labeled "Spectral Contrast Shift" (SCS) calculated on-site and in real-time from both bands, a warning is issued in response to an oil spill or other contaminant on the water surface.

The SCS method was derived by using the spectral ratios between the maximum and minimum values of two bands wherein one band is in the near inferred (NIR) band as follows:

$$SCS=[(L_{max2}/L_{max1})-(L_{min2}/L_{min1})]$$

$L_{max1}/L_{min1}$ are the maximum and minimum spectral radiance values and at an appropriate optical band and in the case of MODIS 250 m resolution band $L_1$=649 nm $L_{max2}$ and $L_{min1}$ are the maximum and minimum spectral radiance values at the NIR band. In the case of MODIS 250 m resolution band $L_2$=869 nm.

The area chosen for inspection should adhere to the following criteria when applying the SCS calculation:
  a. It should include two classes, the suspected oil patch and adjacent clear water patch.
  b. It should be small enough to insure that the two classes are experiencing the same atmospheric conditions i.e. sun, glint, etc.
  c. Cloud shadow should be excluded.

Table 1 shows the SCS value for oil and other contaminants when applying MODIS 250 m resolution bands on suspected patches of water surfaces.

TABLE 1

The SCS values corresponding to different contaminates on the water surface when using the MODIS 250 resolution spectral bands.

| SCS value | Concentration Type |
| --- | --- |
| 0.02 | Ballast water |
| 0.03 | Sheen |
| 0.04 | Oil |
| Values > 0.04 | Other contaminates |

One advantage of this oil spill detector method and system in accordance with the present invention is its ability to identify and call immediate attention to areas where significant contaminants are floating on the water surface.

Figure 1:
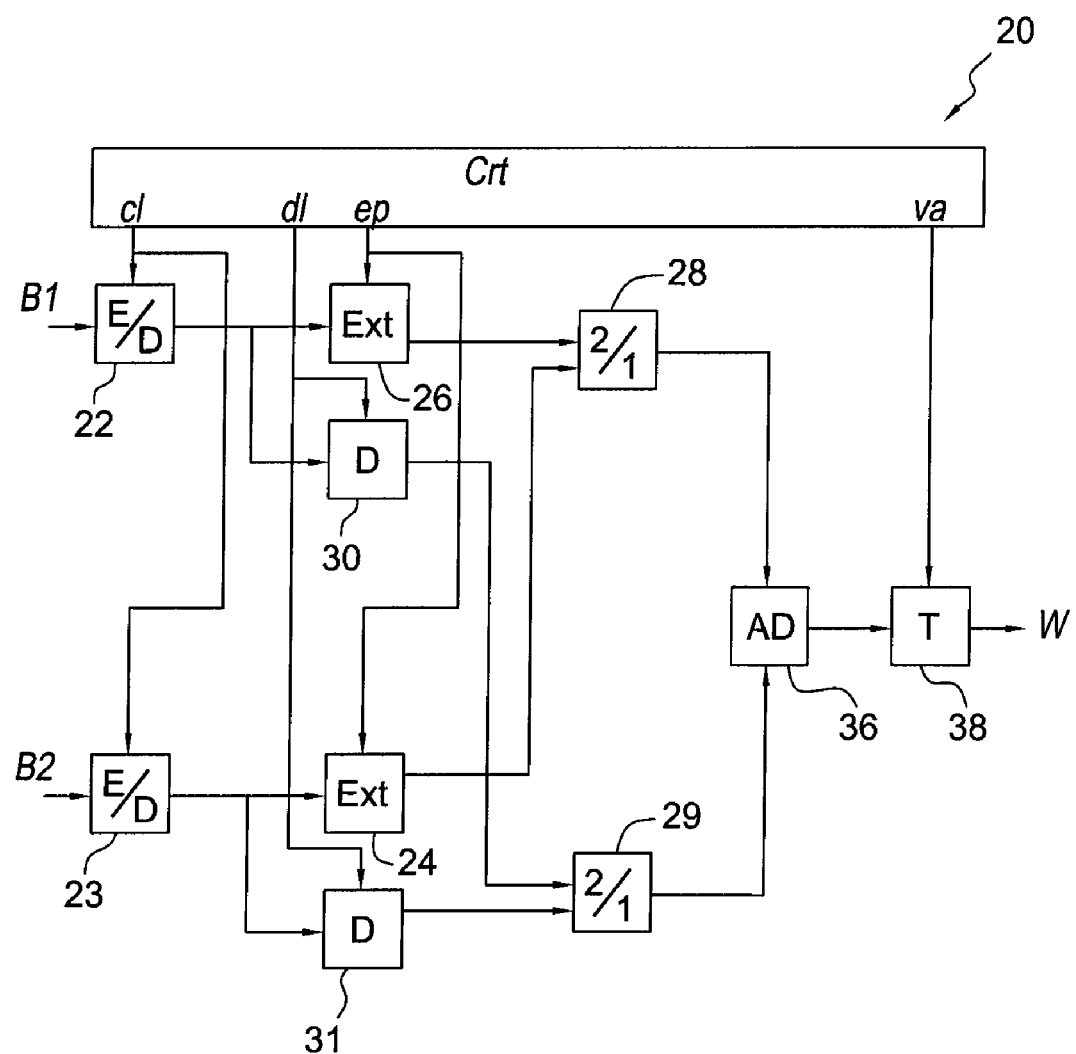
FIG. 1 is a functional block diagram of a method in accordance with one embodiment of the invention.

Referring to FIG. 1, a system 20 includes a pair of enable/disable gates 22 and 23 which receive data inputted from bands $L_1$ and $L_2$ and simultaneously disable at both bands processing data over areas where cloud cover exists. The information for the cloud and land masks (cl) are inputted from an initialization controller 24 that synchronizes the overall system operations. It is also contemplated that the initialization controller 24 can be replaced by an operational computer.

For spaceborne operations, both the land and cloud masks, are necessary. For airborne flights, only the land mask is used, because flights can be conducted at lower altitudes to avoid cloud cover. The land mask data file can be acquired from the University of Maryland Department of Geography who generated the global land cover classification collection in 1998 from the AVHRR satellite imagery acquired between 1981 and 1994. This product is available at three spatial scales: 1 degree, 8 kilometer and 1 kilometer pixel resolutions to distinguish fourteen land cover classes. For the cloud mask, we will employ the MODIS Cloud Mask product (MOD35_L2), which is a Level 2 product generated at 1-km and 250-m (at nadir) spatial resolutions. The algorithm employs a series of visible and infrared threshold and consistency tests to specify confidence that an unobstructed view of the Earth's surface is observed. The 250-m cloud-mask flags are based on the visible channel data only. The MODIS cloud mask provides fifteen classes of cloud cover types.

In the case of cloudless conditions or non-existence of land, the enable/disable gates 22 and 23 enable the band data from bands $L_1$ and $L_2$ to be processed. A pair of extreme value units 26 and 27 calculate the respective values exceeding threshold (ep) from the data flow of each band $L_1$ and $L_2$. A pair of division units or dividers 28 and 29 generates the value ($L_1/L2$) for the extreme and neighboring values respectively.

Neighborhood is defined by a delay unit 30, 31 and delay value (dl) whose value is defined by the initialization controller 24. An absolute value unit 36 calculates the incompatibility/difference values which represent the different behavior of bands $L_1$ and $L_2$ over water surface contaminated by oil or other surface contaminants.

The spectral ratios values after the absolute value unit 36 is $[(L_{max2}/L_{max1}-L_{min2}/L_{min1})]$ where $L_{max1}$ and $L_{min1}$ are the maximum and minimum spectral radiance values at 649 nm, corresponding to MODIS band 1 of the 250 m bands. $L_{max2}$ and $L_{min2}$ are the maximum and minimum spectral radiance values at 869 nm, corresponding to MODIS band 2 of the 250 m bands". A classification table 38 receives a signal from the absolute value unit 36 and based on a comparison with a classification (va) inputted by the initialization controller 24 provides a warning "W" when a contaminant is indicated.

Figure 2:
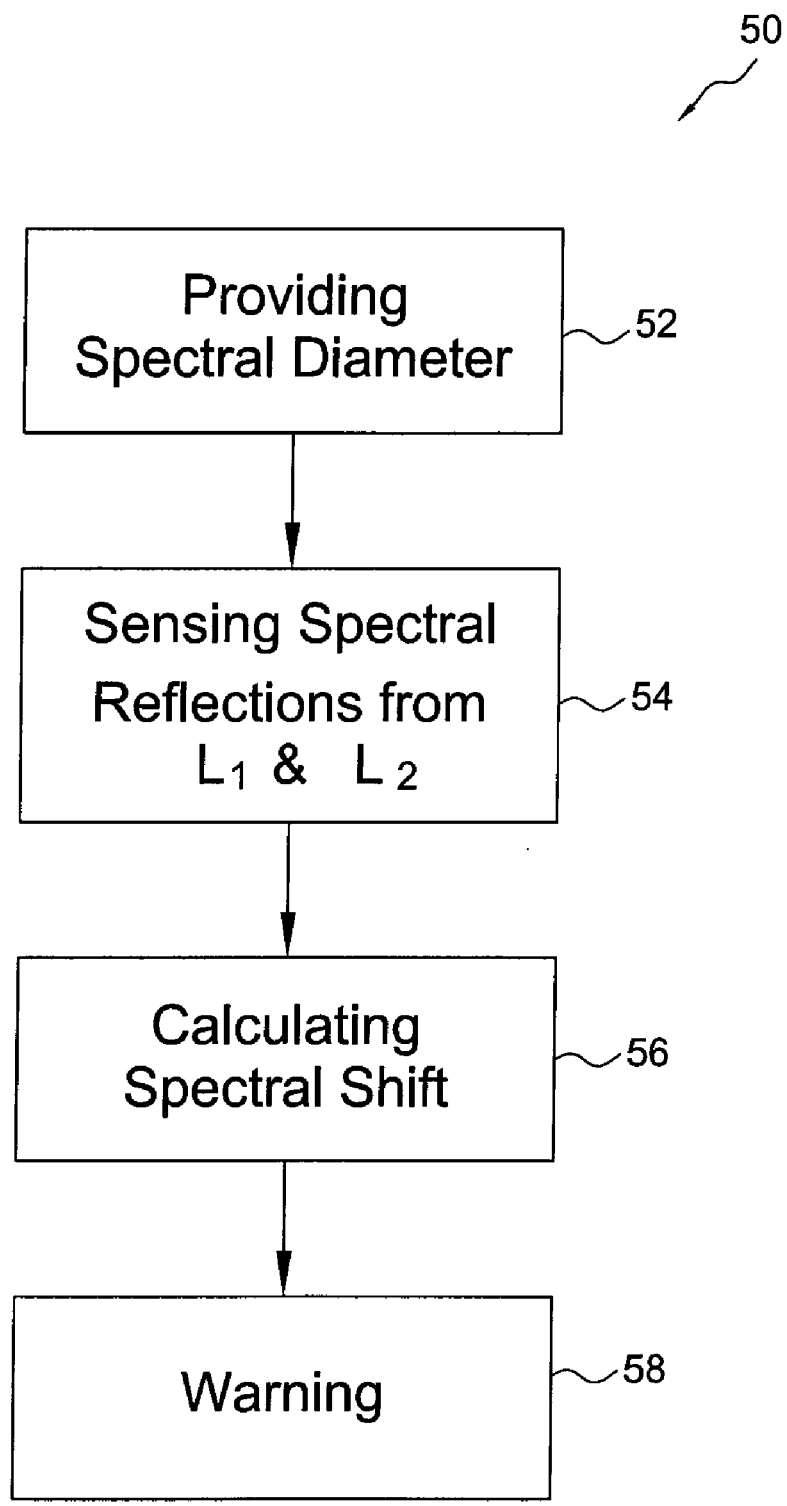
FIG. 2 is a flow chart illustrating the steps in a method in accordance with the present invention.
Figure 3:
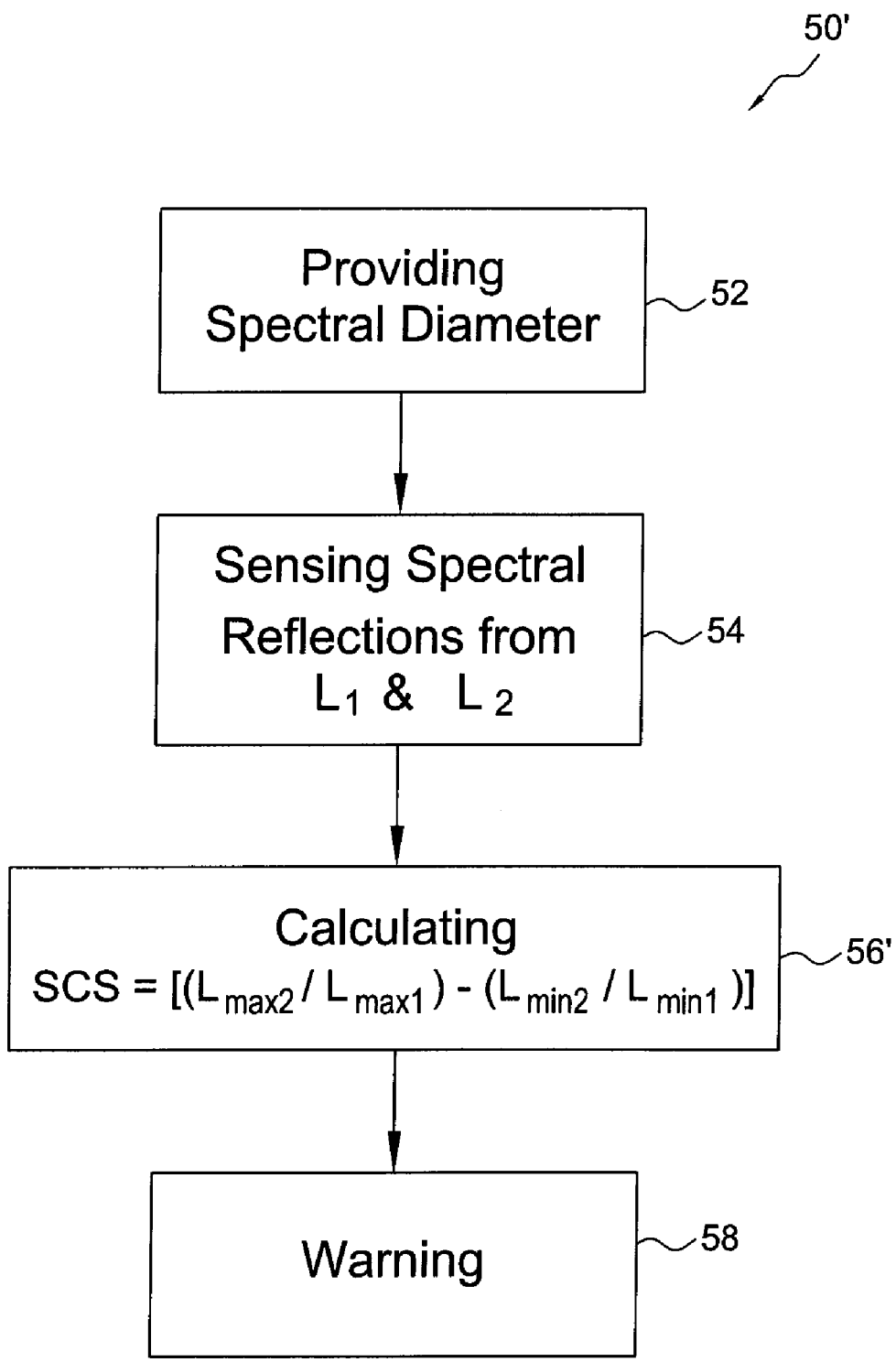
FIG. 3 is a block diagram illustrating a system for detecting oil spills in accordance with the present invention.

An airborne oil spill determination method for detecting oil spills on water surfaces will now be described in connection with FIGS. 2 and 3. As shown in FIGS. 2 and 3 methods 50 and 55 (FIGS. 2 and 3 respectively) each includes the step 52 of providing a moderate-resolution-imaging spectroradiometer for detecting a wide range of electromagnetic resolution. In a preferred embodiment of the invention the moderate-resolution-imaging-spectroradiometer (MODIS) produces two 250 m resolution bands $L_1$ and $L_2$ wherein $L_1$ is 649 mm i.e. within the visual range, while $L_2$ has a wavelength of 869 nm that is within the NIR range.

The method for detecting oil spills or other contaminants on a water surface in accordance with the present invention also includes a step 54 of sensing the spectral reflection from two optical bands wherein one of the bands is within the near inferred range and the other of the bands is within the visual range. In practice, spectral reflections are sensed from two adjacent areas of water. One area is suspected of containing a contaminant and the other adjacent an area of clear water.

An important step in detecting oil spills includes step 56 (FIG. 2) or step 56' (FIG. 3) wherein the spectral contrast shift is calculated on-sight and in real-time from both bands $B_1$ and $B_2$. In the preferred embodiment of the invention (FIG. 3) the spectral contrast shift is calculated using the following equation:

$$SCS=[(L_{max2}/L_{max1})-(L_{min2}/L_{min1})]$$

Wherein $L_{max1}$ and $L_{min1}$ are the maximum and minimum spectral radiance values at an appropriate optical band, and in the case of MODIS 250 m resolution bands, $L_1$=649 nm. $L_{max2}$ and $L_{min2}$ are the maximum and minimum spectral radiance values at the NIR band, and in the case of MODIS 250 m resolution bands, $L_2$=869 nm Finally, in step 58, a warning is issued as for example a visual, audio or printed warning is issued when oil or other contaminant is indicated by a comparison of an absolute value of the differences.

While the invention has been disclosed in connection with its preferred embodiments it should be recognized that changes and modifications may be made therein without departing from the scope of the claims.

What is claimed is:

1. An airborne/spaceborne oil spill determination system for detecting oil spills and other contaminants on a water surface, such systems comprising:
    a moderate resolution imaging spectrometer providing high radiometric sensitivity in two spectral bands $L_1$ and $L_2$ ranging in wavelength from 0.4 µm to 14.4 µm and wherein one of the bands is within the near infrared range and the other of the bands is outside of the near infrared range;
    an initialization controller for synchronizing the system operation and inputting cloud and land masks signals;
    a pair of enabling/disabling gates for receiving data from bands $L_1$ and $L_2$ for simultaneously disabling at both bands processing data over areas where cloud and land masks exists;
    said enable/disable gates enable band data to be processed further when cloudless conditions or the non existence of land exists;
    a pair of extreme value units for calculating the respective extreme values exceeding a programmed threshold from the data flow from $L_1$ and $L_2$;
    an absolute value calculator, a classification table and a warning indicator;
    a pair of delay circuits for inputting a delay value "dl" that is defined by said initialization controller; and
    a pair of division members for generating values of bands $L_1$ and $L_2$ for the extreme enabling values respectively and for feeding signals to said absolute value calculator; and
    wherein said absolute value calculator calculates the incompatibility/difference value which represents the different behavior of bands $L_1$ and $L_2$ over a water surface contaminated by oil or other surface contaminant and the spectral ratio values after the absolute value calculated are $[(L_{max2}/L_{max1} - L_{min2}/L_{min1})]$ wherein $L_{max1}$ and $L_{min1}$ are the maximum and minimum spectral radiance values at 649 nm, corresponding to MODIS band 1 of the 250 m bands. $L_{max2}$ and $L_{min2}$ are the maximum and minimum spectral radiance values at 869 nm, corresponding to MODIS band 2 of the 250 m bands;
    whereby said classification table produces a warning "W" based on the programmed classes from the classification value (va) inputted by said utilization controller.

2. An airborne/spaceborne oil spill determination system for detecting oil spills and other contaminants on a water surface, such systems consisting of:
    a moderate resolution imaging spectrometer providing high radiometric sensitivity in two spectral bands $L_1$ and $L_2$ ranging in wavelength from 0.4 µm to 14.4 µm and wherein one of the bands is within the near infrared range and the other of the bands is outside of the infrared range;
    an initialization controller for synchronizing the system operation and inputting cloud and land masks signals;
    a pair of enabling/disabling gates for receiving data from bands $L_1$ and $L_2$ for simultaneously disabling at both bands processing data over areas where cloud cover and land exists;
    said enable/disable gates enable band data to be processed further when cloudless conditions exists or the non-existence of land;
    a pair of extreme value units for calculating the respective extreme values exceeding a programmed threshold from the data flow from $L_1$ and $L_2$;
    an absolute value calculator, a classification table and a warning indicator;
    a pair of delay circuits for inputting a delay value "dl" that is defined by said initialization controller; and
    a pair of division members for generating values of bands $L_1$ and $L_2$ for the extreme enabling values respectively and for feeding signals to said absolute value calculator; and
    wherein said absolute value calculator calculates the incompatibility/difference value which represents the different behavior of bands $L_1$ and $L_2$ over a water surface contaminated by oil or other surface contaminant and the spectral ratio values after the absolute value calculated are $[(L_{max2}/L_{max1} - L_{min2}/L_{min1})]$ wherein $L_{max\,1}$ and $L_{min1}$ are the maximum and minimum spectral radiance values at 649 nm, corresponding to MODIS band 1 of the 250 m bands. $L_{max2}$ and $L_{min2}$ are the maximum and minimum spectral radiance values at 869 nm, corresponding to MODIS band 2 of the 250 m bands;
    whereby said classification table produces a warning "W" based on the programmed classes from the classification value (va) inputted by said utilization controller.

* * * * *